United States Patent
Brown

(10) Patent No.: US 10,932,807 B2
(45) Date of Patent: Mar. 2, 2021

(54) ASSEMBLY TOOL FOR ULTRASONIC SURGICAL INSTRUMENTS AND KITS AND METHODS INCLUDING THE SAME

(71) Applicant: COVIDIEN LP, Mansfield, MA (US)

(72) Inventor: Michael J. Brown, Superior, CO (US)

(73) Assignee: COVIDIEN LP, Mansfield, MA (US)

( * ) Notice: Subject to any disclaimer, the term of this patent is extended or adjusted under 35 U.S.C. 154(b) by 621 days.

(21) Appl. No.: 15/427,143

(22) Filed: Feb. 8, 2017

(65) Prior Publication Data
US 2018/0221047 A1   Aug. 9, 2018

(51) Int. Cl.
A61B 17/00   (2006.01)
A61B 17/32   (2006.01)
A61B 17/29   (2006.01)

(52) U.S. Cl.
CPC .......... *A61B 17/320068* (2013.01); *A61B 17/320092* (2013.01); *A61B 2017/00477* (2013.01); *A61B 2017/00526* (2013.01); *A61B 2017/00734* (2013.01); *A61B 2017/2929* (2013.01)

(58) Field of Classification Search
CPC .... A61B 17/320068; A61B 17/320092; A61B 2017/00477; A61B 2017/00526; A61B 2017/00734; A61B 2017/2929
USPC ................................................. 29/594, 592.1
See application file for complete search history.

(56) References Cited

U.S. PATENT DOCUMENTS

| | | |
|---|---|---|
| 5,057,119 A | 10/1991 | Clark et al. |
| 5,059,210 A | 10/1991 | Clark et al. |
| 5,776,155 A | 7/1998 | Beaupre et al. |
| 5,996,453 A | 12/1999 | Blacklock |
| 6,499,358 B1 | 12/2002 | Hogan et al. |
| 6,611,240 B2 | 8/2003 | Robinson |
| 6,716,028 B2 | 4/2004 | Rahman et al. |
| 8,114,104 B2 | 2/2012 | Young et al. |
| 8,231,644 B2 | 7/2012 | Onaga |
| 8,435,258 B2 | 5/2013 | Young et al. |

(Continued)

FOREIGN PATENT DOCUMENTS

| | | |
|---|---|---|
| EP | 1897502 A1 | 3/2008 |
| EP | 2484290 A1 | 8/2012 |

(Continued)

OTHER PUBLICATIONS

Extended European Search Report issued in corresponding EP application No. 18155475.9 dated Mar. 29, 2018, 7 pages.

*Primary Examiner* — Peter Dungba Vo
*Assistant Examiner* — Azm A Parvez

(57) ABSTRACT

An assembly tool for use with an ultrasonic surgical instrument includes a body portion, a neck, and a head portion. The body portion includes a base and first and second legs extending from the base to define a receiving area therebetween. The neck is attached to the body portion and the head portion is attached to the neck. The head portion defines a central opening. The first and second legs of the body portion are configured to engage a portion of a housing of an ultrasonic surgical instrument received within the receiving area, and the head portion is configured to engage a rotation knob of the ultrasonic surgical instrument received within the central opening to rotationally fix the rotation knob relative to the housing. Kits including the assembly tool and methods of assembling an ultrasonic surgical instrument using the assembly tool are also provided.

17 Claims, 5 Drawing Sheets

(56) References Cited

U.S. PATENT DOCUMENTS

| | | |
|---|---|---|
| 8,834,465 B2 | 9/2014 | Ramstein et al. |
| 8,845,541 B2 | 9/2014 | Strunk et al. |
| 9,113,913 B2 | 8/2015 | Reeve |
| 2006/0229627 A1 | 10/2006 | Hunt et al. |
| 2009/0206130 A1* | 8/2009 | Hall ................ A61B 17/07207 227/175.2 |
| 2010/0062390 A1 | 3/2010 | Hetsroni |
| 2012/0116388 A1* | 5/2012 | Houser ............ A61B 17/00234 606/41 |
| 2013/0090577 A1 | 4/2013 | Boudreaux et al. |
| 2015/0245850 A1* | 9/2015 | Hibner ............... A61B 18/1482 606/171 |

FOREIGN PATENT DOCUMENTS

| | | |
|---|---|---|
| EP | 2484301 B1 | 6/2016 |
| WO | 2017/066087 A1 | 4/2017 |

\* cited by examiner

ASSEMBLY TOOL FOR ULTRASONIC SURGICAL INSTRUMENTS AND KITS AND METHODS INCLUDING THE SAME

BACKGROUND

Technical Field

The present disclosure relates to surgical instruments and, more particularly, to an assembly tool for facilitating assembly of an ultrasonic surgical instrument, kits including the assembly tool, and methods of assembly using the assembly tool.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, and/or fulgurate tissue to effect hemostasis.

Ultrasonic surgical instruments typically employ a transducer that produces ultrasonic energy for transmission along a waveguide to an end effector designed to treat tissue with the ultrasonic energy. Some ultrasonic surgical instruments include a transducer and/or waveguide that is removable and, thus, requires releasable engagement of the transducer and waveguide. In such configurations, the transducer and waveguide should be sufficiently secured to one another during assembly to maintain the engagement therebetween during use and to ensure proper operation.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is an assembly tool for use with an ultrasonic surgical instrument including a housing and a rotation knob rotatable relative to the housing. The assembly tool includes a body portion, a neck attached to the body portion, and a head portion attached to the neck. The body portion includes a base and first and second legs extending from the base to define a receiving area therebetween. The head portion defines a central opening. The first and second legs of the body portion are configured to engage a portion of a housing of an ultrasonic surgical instrument received within the receiving area while the head portion is configured to engage a rotation knob of the ultrasonic surgical instrument received within the central opening to rotationally fix the rotation knob relative to the housing.

In aspects of the present disclosure, the head portion of the assembly tool includes first and second arms cooperating to define the central opening therebetween. The first and second arms include free ends defining a mouth therebetween that provides access to the central opening. The first and second arms may be movable to vary a width of the mouth. Additionally or alternatively, the mouth may be positioned to oppose the neck.

In aspects of the present disclosure, the head portion of the assembly tool includes an interior surface surrounding the central opening and configured complementary to an exterior surface of the rotation knob of the ultrasonic surgical instrument. The interior surface may include, for example, a plurality of alternating recesses and protrusions.

In aspects of the present disclosure, the receiving area of the body portion of the assembly tool is configured complementary to the portion of the housing of the ultrasonic surgical instrument configured for receipt within the receiving area.

In aspects of the present disclosure, the body portion, the neck, and the head are a single, monolithic component.

A kit provided in accordance with aspects of the present disclosure includes an ultrasonic surgical instrument including a housing and a rotation knob rotatable relative to the housing and an assembly tool according to any of the aspects above or otherwise herein. The assembly tool is releasably engagable with the ultrasonic surgical instrument to rotationally fix the rotation knob relative to the housing.

In aspects of the present disclosure, the ultrasonic surgical instrument includes an outer sleeve extending distally from the housing. The outer sleeve is configured to pass through the mouth of the head portion of the assembly tool and into the central opening of the assembly tool to enable engagement of the head portion of the assembly tool with the rotation knob of the ultrasonic surgical instrument. The first and second arms of the head portion of the assembly tool may be configured to move to vary a width of the mouth to facilitate passage of the outer sleeve of the ultrasonic surgical instrument through the mouth. Additionally or alternatively, the first and second arms may be configured to move to engage the rotation knob under bias.

In aspects of the present disclosure, the rotation knob includes a plurality of spaced-apart flutes defined on the exterior surface thereof, and an interior surface of the head portion of the assembly tool defines a plurality of spaced-apart protrusions configured for respective receipt within the plurality of spaced-apart flutes of the rotation knob of the ultrasonic surgical instrument.

In aspects of the present disclosure, the receiving area of the body portion of the assembly tool is configured complementary to the portion of the housing of the ultrasonic surgical instrument.

In aspects of the present disclosure, the first and second legs of the body portion of the assembly tool are configured to move to vary a width of the receiving area of the body portion of the assembly tool to facilitate receipt of the portion of the housing of the ultrasonic surgical instrument within the receiving area of the body portion of the assembly tool. Additionally or alternatively, the first and second legs of the body portion of the assembly tool may be configured to move to engage the portion of the housing of the ultrasonic surgical instrument received within the receiving area of the body portion of the assembly tool under bias.

A method of assembling an ultrasonic surgical instrument provided in accordance with aspects of the present disclosure includes positioning a threaded connector of a waveguide adjacent a threaded connector of an ultrasonic transducer with the waveguide and the ultrasonic transducer supported by a housing. The waveguide includes a rotation knob operably associated therewith and configured to rotate the waveguide relative to the housing. The method further includes engaging an assembly tool with the rotation knob and a portion of the housing such that the rotation knob is maintained in fixed rotational orientation relative to the housing, and rotating the ultrasonic transducer relative to the housing to engage the threaded connector of the ultrasonic transducer with the threaded connector of the waveguide.

In aspects of the present disclosure, positioning the threaded connector of the waveguide adjacent the threaded connector of the ultrasonic transducer with the waveguide and the ultrasonic transducer supported by the housing includes inserting the ultrasonic transducer onto or into the housing. Additionally or alternatively, positioning the threaded connector of the waveguide adjacent the threaded connector of the ultrasonic transducer with the waveguide and the ultrasonic transducer supported by the housing includes inserting the waveguide into the housing.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and.

DETAILED DESCRIPTION

Figure 1:
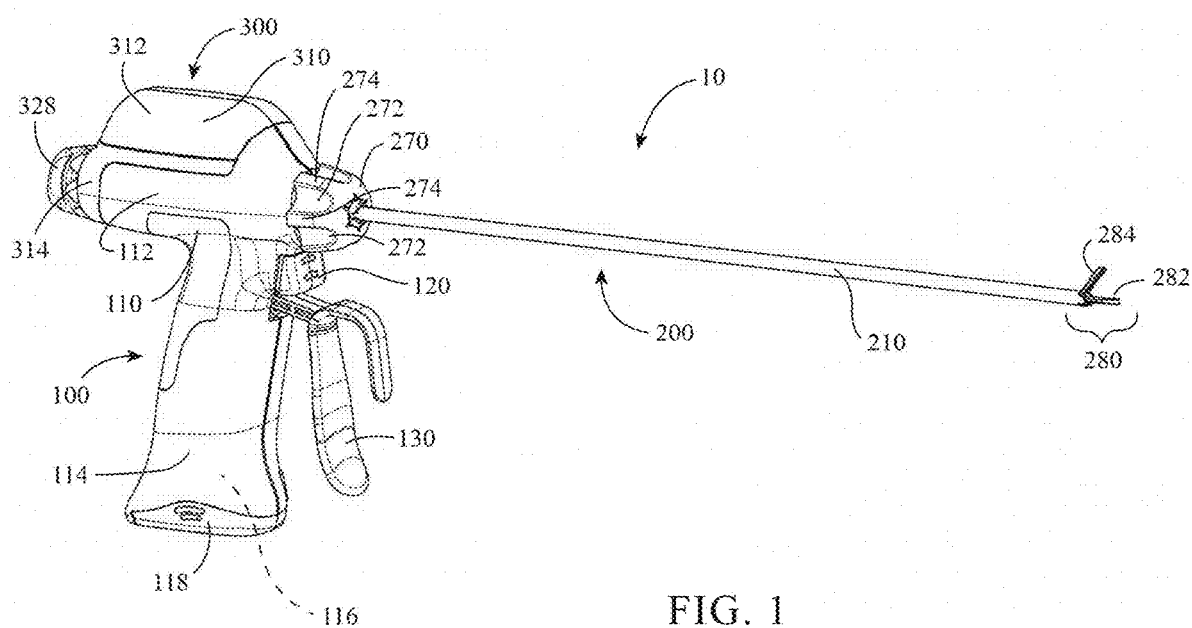
FIG. 1 is a side, perspective view of an ultrasonic surgical instrument.
Figure 2:
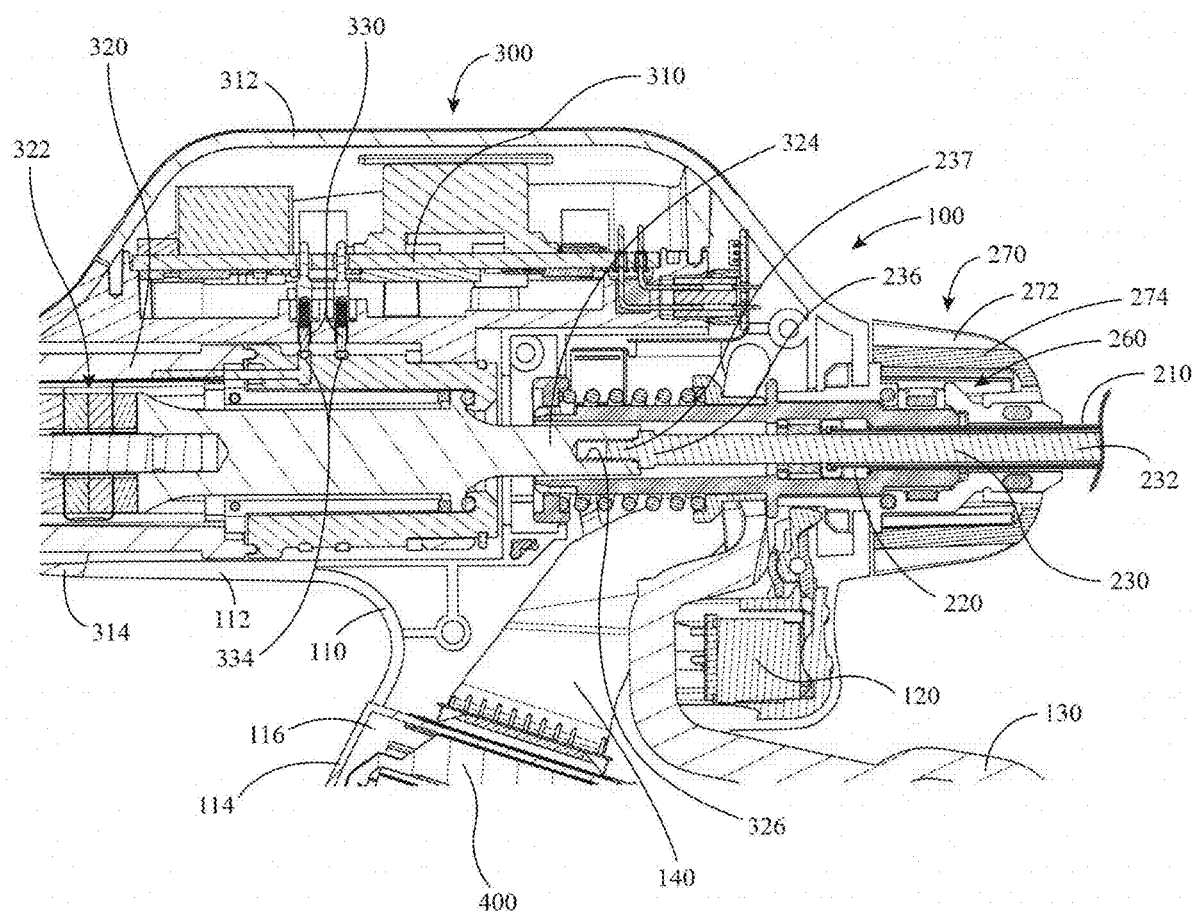
FIG. 2 is an enlarged, side, longitudinal, cross-sectional view of a proximal portion of the ultrasonic surgical instrument of FIG. 1.
Figure 3:
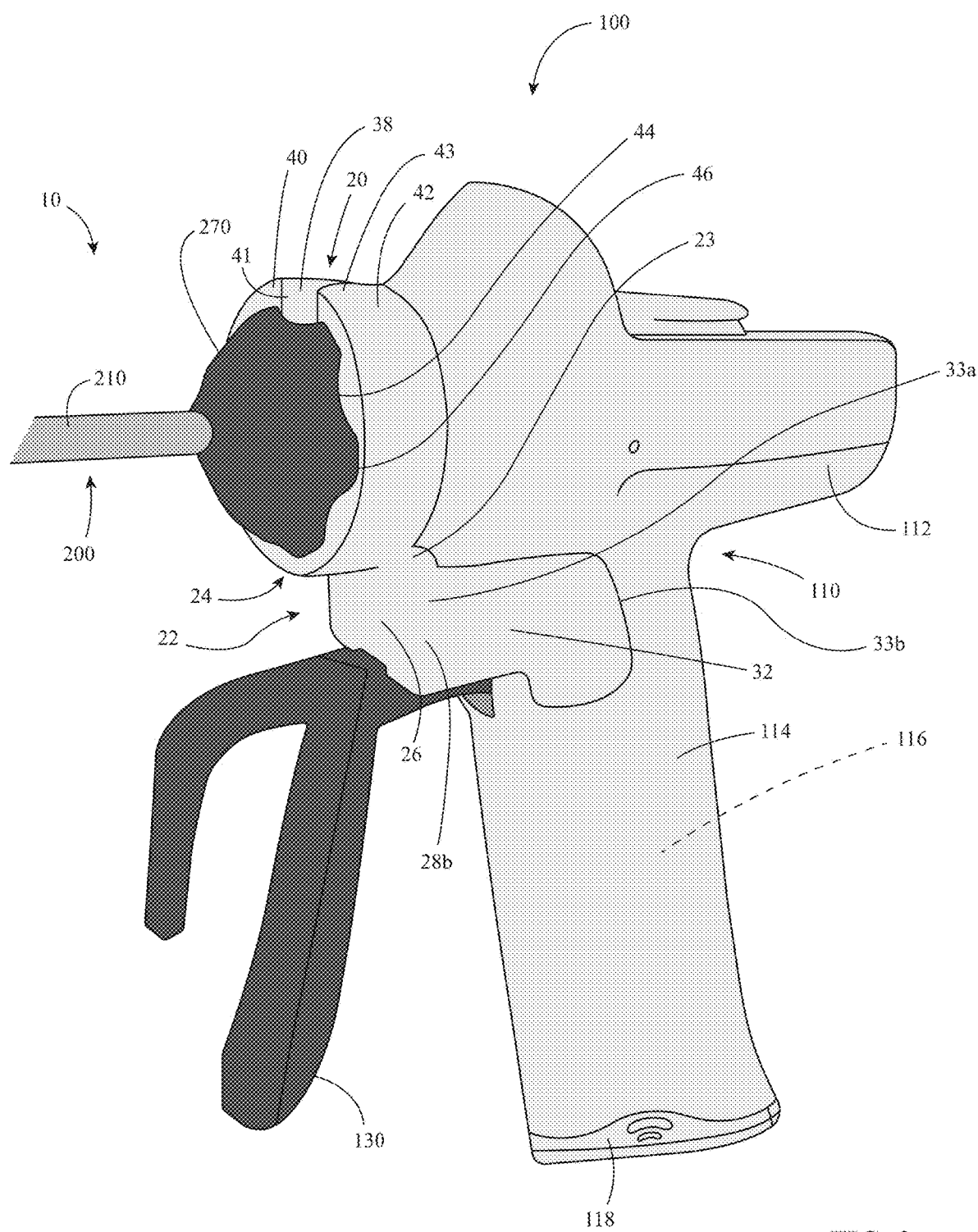
FIG. 3 is a side, perspective view of a proximal portion of the ultrasonic surgical instrument of FIG. 1 with the transducer and generator assembly ("TAG") removed therefrom and an assembly tool provided in accordance with the present disclosure operably engaged therewith.
Figure 4A:
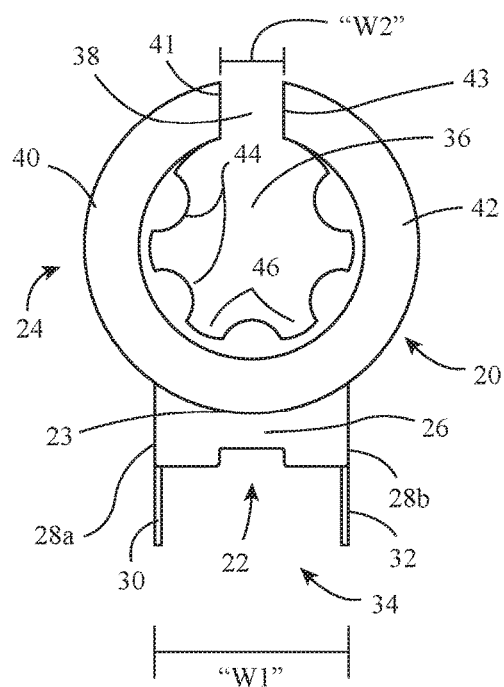
FIG. 4A is a front view of the assembly tool of FIG. 3.
Figure 4B:
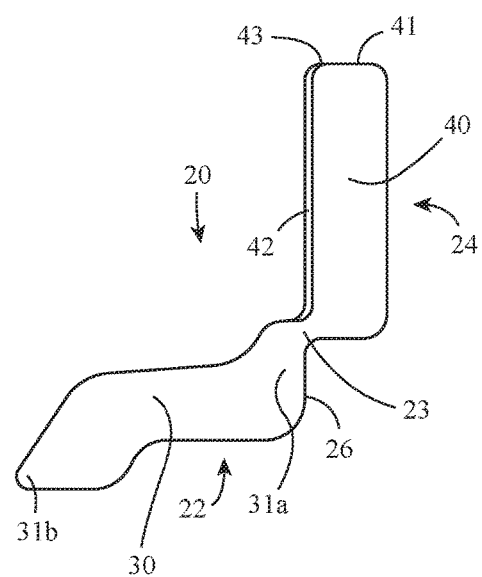
FIG. 4B is a side view of the assembly tool of FIG. 3.
Figure 4C:
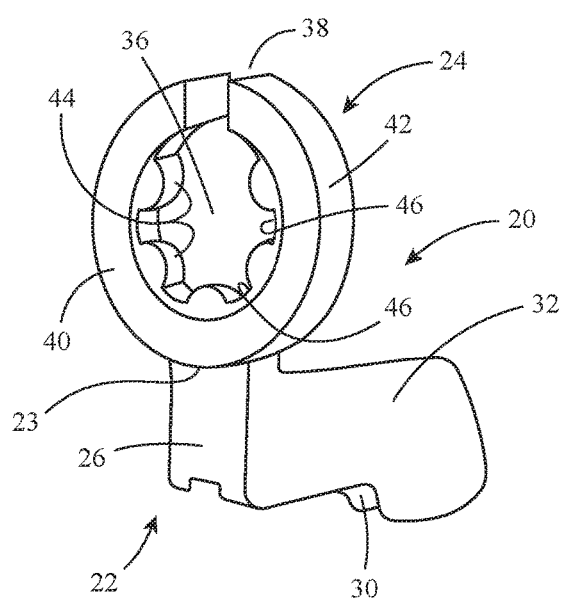
FIG. 4C is a perspective view of the assembly tool of FIG. 3.

Referring generally to FIGS. 1-3, the present disclosure relates to an assembly tool 20 (FIG. 3) configured to facilitate assembly of an ultrasonic surgical instrument such as, for example, ultrasonic surgical instrument 10. Although assembly tool 20 (FIG. 3) is detailed herein for use in conjunction with ultrasonic surgical instrument 10, assembly tool 20 (FIG. 3) may likewise be used in conjunction with any suitable ultrasonic surgical instrument to facilitate assembly thereof. For the purposes herein, ultrasonic surgical instrument 10 is generally described. Ultrasonic surgical instrument 10 is described in greater detail in U.S. Provisional Patent Application No. 62/332,028, filed on May 5, 2016, the entire contents of which are hereby incorporated herein by reference.

Referring to FIGS. 1 and 2, ultrasonic surgical instrument 10 includes a handle assembly 100 and an elongated assembly 200 that is configured to releasably engage handle assembly 100, although elongated assembly 200 may alternatively be permanently engaged with handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support an ultrasonic transducer and generator assembly ("TAG") 300 including a generator 310 and an ultrasonic transducer 320. TAG 300 may be permanently engaged with body portion 112 of housing 110 or removable therefrom. Generator 310 includes a housing 312 configured to house the internal electronics of generator 310, and a cradle 314 configured to rotatably support ultrasonic transducer 320. Ultrasonic transducer 320 includes a piezoelectric stack 322 and a distally-extending horn 324. Horn 324 defines a threaded female receiver 326. A set of connectors 330 and corresponding rotational contacts 334 associated with generator 310 and ultrasonic transducer 320, respectively, enable drive signals to be communicated from generator 310 to piezoelectric sack 322 of ultrasonic transducer 320 to drive ultrasonic transducer 320. Ultrasonic transducer 320 further includes a rotation knob 328 extending proximally therefrom that, when rotated, rotates ultrasonic transducer 320 relative to generator 310 and housing 110. As detailed below, rotation knob 328 facilitates engagement of ultrasonic transducer 320 with waveguide 230 of elongated assembly 200.

With reference to FIG. 2, fixed handle portion 114 of housing 110 defines a compartment 116 configured to receive a battery assembly 400 and a door 118 configured to enclose compartment 116. An electrical connection assembly 140 is disposed within housing 110 of handle assembly 100 and serves to electrically couple activation button 120, generator 310 of TAG 300, and battery assembly 400 with one another when TAG 300 is supported on or in body portion 112 of housing 110 and battery assembly 400 is disposed within compartment 116 of fixed handle portion 114 of housing 110, thus enabling activation of ultrasonic surgical instrument 10 in response to depression of activation button 120.

Referring still to FIGS. 1 and 2, elongated assembly 200 includes an outer drive sleeve 210, an inner support sleeve 220 disposed within outer drive sleeve 210, a waveguide 230 extending through inner support sleeve 220, a drive assembly 250, an integrated torque assembly 260, a rotation knob 270, and an end effector 280 including a blade 282 and a jaw 284. A proximal portion of outer drive sleeve 210 is operably coupled to clamp trigger 130 of handle assembly 100 via drive assembly 250, while a distal portion of outer drive sleeve 210 is operably coupled to jaw 284. As such, clamp trigger 130 is selectively actuatable to thereby move outer drive sleeve 210 about inner support sleeve 220 to pivot jaw 284 relative to blade 282 of end effector 280 from a spaced-apart position to an approximated position for clamping tissue between jaw 284 and blade 282. Drive assembly 250 provides a force-limiting feature whereby the clamping pressure applied to tissue is limited to a particular clamping pressure or particular clamping pressure range. Rotation knob 270 defines a plurality of spaced-apart flutes 272 arranged annularly about an exterior surface of rotation knob 270. As a result of this configuration, rotation knob 270 defines alternating flutes 272 and protrusions 274 arranged annularly thereabout. This configuration facilitates rotation of rotation knob 270, e.g., with a single finger. Flutes 272 define arcuate configurations, while protrusions 274 are squared-off; however, other configurations are also contemplated.

Waveguide 230, as noted above, extends through inner support sleeve 220. Waveguide 230 defines a body 232 and a blade 282 extending from the distal end of body 232. Blade 282 serves as the blade of end effector 280. Waveguide 230 further includes a proximal connector 236 configured to enable engagement of waveguide 230 with horn 324 of ultrasonic transducer 320 such that ultrasonic motion produced by ultrasonic transducer 320 is transmitted along waveguide 230 to blade 282 for treating tissue clamping between blade 282 and jaw 284 or positioned adjacent to blade 282. To this end, proximal connector 236 includes a threaded male shaft 237 that is configured for threaded engagement within threaded female receiver 326 of horn 324 of ultrasonic transducer 320.

As can be appreciated, waveguide 230 and ultrasonic transducer 320 should be sufficiently engaged with one another to maintain the engagement therebetween during use and to ensure proper operation, without over-tightening the engagement between threaded male shaft 237 and threaded female receiver 326. Integrated torque assembly 260 helps ensure that waveguide 230 and ultrasonic transducer 320 are sufficiently engaged while inhibiting over-tightening. More specifically, integrated torque assembly 260 is operably coupled about outer drive sleeve 210, inner support sleeve 220, and waveguide 230 such that rotation of rotation knob 270 relative to handle assembly 100 rotates elongated assembly 200 relative to handle assembly 100 up to a torque threshold, at which point integrated torque assembly 260 decouples rotation knob 270 from the other components of elongated assembly 200 such that further rotation of rotation knob 270 does not impart rotation to the other components of elongated assembly 200.

Referring generally to FIGS. 1 and 2, in order to engage threaded male shaft 237 and threaded female receiver 326 with one another to thereby engage waveguide 230 and ultrasonic transducer 320 with one another, rotation knob 328 of ultrasonic transducer 320 or rotation knob 270 of elongated assembly 200 is held in fixed rotational position, while the other rotation knob 328, 270 is rotated to thereby establish relative rotation between threaded male shaft 237 and threaded female receiver 326 to progressively engage threaded male shaft 237 and threaded female receiver 326 with one another. When sufficient engagement is achieved, integrated torque assembly 260 "slips" such that, upon further application of torque, threaded male shaft 237 and threaded female receiver 326 rotate together with one another, inhibiting further engagement therebetween. As an alternative to integrated torque assembly 260, a separate torque wrench (not shown), for example, positionable about rotation knob 328 and utilized to rotate rotation knob 328 relative to rotation knob 270 until the torque wrench (not shown) "slips" and inhibits further rotation of rotation knob 328, may be provided. In either configuration, assembly tool 20, as detailed below with reference to FIGS. 3-5B, is configured to facilitate the engagement of threaded male shaft 237 and threaded female receiver 326 with one another, thus facilitating the engagement of waveguide 230 and ultrasonic transducer 320 with one another.

Referring to FIGS. 3 and 4A-4C, assembly tool 20 includes a body portion 22, a neck 23, and a head portion 24. Assembly tool 20 may be monolithically formed, e.g., via injection molding, from a suitable plastic, although other formation methods and/or materials are also contemplated. Body portion 22 of assembly tool 20 includes a base 26 and first and second legs 30, 32. Base 26 defines first and second end portions 28a, 28b. Fixed ends 31a, 33a of first and second legs 30, 32 are attached, e.g., formed with, base 26 at first and second end portions 28a, 28b, respectively, of base 26. First and second legs 30, 32 extend from fixed ends 31a, 33a to free ends 31b, 33b, respectively, thereof, such that body portion 22 of assembly tool 20 defines a substantially U-shaped configuration. More specifically, first and second legs 30, 32 extend in substantially perpendicular orientation relative to base 26, e.g., within about 15 degrees of perpendicular, and are disposed in substantially parallel orientation relative to one another, e.g., within about 15 degrees of parallel.

As a result of the above-detailed configuration, body portion 22 of assembly tool 20 defines a U-shaped receiving area 34 having a width "W1." Width "W1" generally approximates the width of a portion of fixed handle portion 114 of housing 110 of handle assembly 100 of ultrasonic surgical instrument 10 so as to enable receipt of the portion of fixed handle portion 114 within receiving area 34. Further, with legs 30, 32 of body portion 22 attached to base 26 at fixed ends 31a, 33a, respectively, thereof, and extending to free ends 31b, 33b, respectively, thereof, legs 30, 32 define cantilever configurations enabling flexion of legs 30, 32 towards and away from one another to vary the width "W1" of receiving area 34. In some embodiments, width "W1" may be slightly smaller than the width of the portion of fixed handle portion 114 of housing 110 of handle assembly 100 such that body portion 22 is retained in position about the portion of fixed handle portion 114 under the bias of cantilever legs 30, 32 towards an at-rest position. It is also contemplated that legs 30, 32 define inner surface features that complement outer surface features of the portion of fixed handle portion 114 of housing 110 of handle assembly 100 so as to enable complementary-fit engagement of body portion 22 of assembly tool 20 about fixed handle portion 114 of housing 110 of handle assembly 100.

Body portion 22 of assembly tool 20, as detailed above, is configured for use with ultrasonic surgical instrument 10 and, thus, is configured complementarily thereto. Depending upon the particular ultrasonic surgical instrument (or instruments) for which assembly tool 20 is configured for use, the above-noted featured of assembly tool 20 may be varied. For example, with respect to ultrasonic surgical instruments having housing portions defining more V-shaped or C-shaped configurations, body portion 22 of assembly tool 20 may be configured such that receiving area 34 defines a more V-shaped or C-shaped configuration. Likewise, the width "W1" may be varied in accordance with the dimensions of the portion of the housing of the particular ultrasonic surgical instrument (or instruments) for which assembly tool 20 is configured for use.

Continuing with reference to FIGS. 3 and 4A-4C, head portion 24 of assembly tool 20 is attached to body portion 22 of assembly tool 20 by way of neck 23 and extends in generally perpendicular orientation relative to legs 30, 32 of body portion 22. Head portion 24 defines a C-shaped configuration having a generally circular central opening 36 and a mouth 38 providing access to central opening 36, although, in other embodiments, head portion 24 may define a closed, O-shaped configuration. Mouth 38 defines a width "W2" and is disposed opposite the attachment of head portion 24 to neck 23 such that C-shaped head portion 24 defines a pair of substantially similar arms 40, 42 attached to one another adjacent neck 23 and spaced-apart from one another at the free ends 41, 43, respectively, thereof to define mouth 38 therebetween. Arms 40, 42 are arcuate so as to define generally circular central opening 36 therebetween, although other configurations are also contemplated. Arms 40, 42 define cantilever configurations enabling flexion of arms 40, 42 towards and away from one another to vary the width "W2" of mouth 38.

The interior surfaces of arms 40, 42 that surround central opening 36 complement the exterior annular surface of rotation knob 270 of ultrasonic surgical instrument 10. More specifically, the interior surfaces of arms 40, 42 include a plurality of alternating protrusions 44 and recesses 46. Protrusions 44 define arcuate configurations and are configured for complementary receipt within flutes 272 of rotation knob 270, while recesses 46 are squared-off so as to complementarily receive protrusions 274 of rotation knob 270. Other configurations complementary to a particular rotation knob configuration, or universal for use with a plurality of different rotation knob configurations, are also contemplated. Further, head portion 24 of assembly tool 20 may be dimensioned relative to rotation knob 270 such that the cantilever configurations of arms 40, 42 help maintain arms 40, 42 in engagement about rotation knob 270 under the bias of arms 40, 42 towards an at-rest position.

With reference to FIGS. 2, 3, and 5A-5B, the use of assembly tool 20 to facilitate engagement of waveguide 230 and ultrasonic transducer 320 with one another is detailed. Initially, TAG 300 is slid onto or into housing 110 of handle assembly 100 such that TAG 300 is supported thereon or therein and such that threaded male shaft 237 of waveguide 230 is positioned adjacent threaded female receiver 326 of ultrasonic transducer 320. As can be appreciated, in configurations where elongated assembly 200 is removable from handle assembly 100, elongated assembly 200 may alternatively be inserted into housing 110 such that elongated assembly 200 is supported by handle assembly 100 and such that threaded male shaft 237 of waveguide 230 is positioned adjacent threaded female receiver 326 of ultrasonic transducer 320.

With threaded male shaft 237 of waveguide 230 positioned adjacent threaded female receiver 326 of ultrasonic transducer 320, or prior thereto, assembly tool 20 is engaged with ultrasonic surgical instrument 10. In order to engage assembly tool 20 with ultrasonic surgical instrument 10, head portion 24 of assembly tool 20 is slid proximally over end effector 280 and outer drive sleeve 210 of elongated assembly 200 with end effector 280 and outer drive sleeve 210 passing through central opening 36 of head portion 24. Alternatively, assembly tool 20 may be positioned about elongated assembly 200 by passing outer drive sleeve 210 through mouth 38 and into central opening 36 of head portion 24 of assembly tool 20.

Once assembly tool 20 is disposed about elongated assembly 200 with outer drive sleeve 210 extending through central opening 36, assembly tool 20 is translated proximally relative to ultrasonic surgical instrument 10 such that body portion 22 of assembly tool 20 is engaged about housing 110 of handle assembly 100 of ultrasonic surgical instrument 10 and such that head portion 24 of assembly tool 20 is engaged about rotation knob 270 of elongated assembly 200 of ultrasonic surgical instrument 10. More specifically, with respect to the engagement of body portion 22 about housing 110, assembly tool 20 is translated proximally relative to housing 110 such that a portion of fixed handle portion 114 of housing 110 is received within receiving area 34 of body portion 22 with cantilever legs 30, 32 of body portion 22 of assembly tool 20 engaging the portion of fixed handle portion 114 of housing 110 on either side thereof.

With respect to the engagement of head portion 24 about rotation knob 270, assembly tool 20 is translated proximally relative to rotation knob 270 such that protrusions 44 of head portion 24 of assembly tool 20 are received within flutes 272 of rotation knob 270 and such that recesses 46 of head portion 24 of assembly tool 20 receive protrusions 274 of rotation knob 270. With head portion 24 of assembly tool 20 positioned in this manner, cantilever arms 40, 42 of head portion 24 of assembly tool 20 engage rotation knob 270 annularly thereabout. It is contemplated that the engagement of body portion 22 of assembly tool 20 with housing 110 of handle assembly 100 and the engagement of head portion 24 of assembly tool 20 with rotation knob 270 occur substantially simultaneously with one another as assembly tool 20 is translated proximally, although other configurations are also contemplated.

With assembly tool 20 engaged about ultrasonic surgical instrument 10 as detailed above, rotation knob 270 is maintained in fixed rotational orientation relative to housing 110 of ultrasonic surgical instrument 10 due to the engagement of legs 30, 32 about housing 110 and the engagement of arms 40, 42 about rotation knob 270. Thus, threaded male shaft 237 of waveguide 230 is maintained in fixed rotational orientation relative to housing 110 (in the absence of excess torque applied to rotation knob 270 so as to cause integrated torque assembly 260 to "slip") without the need for the user to grasp and maintain rotation knob 270 in fixed rotational orientation relative to housing 110.

Figure 5A:
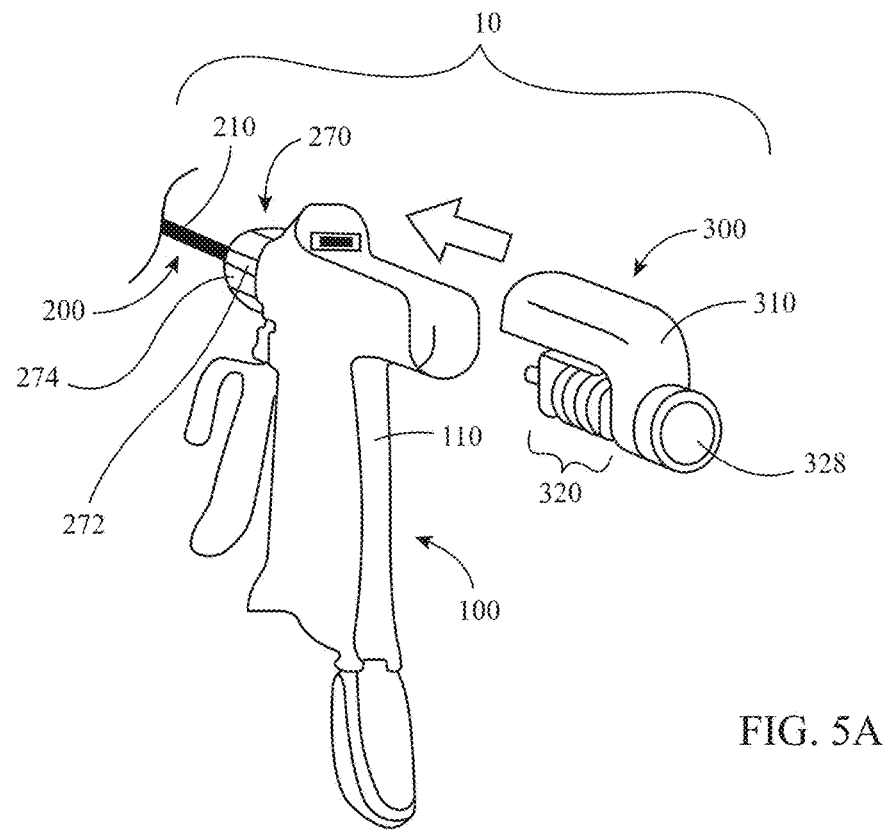
FIG. 5A is a rear, perspective view of the ultrasonic surgical instrument of FIG. 1 illustrating insertion of the TAG into engagement with the ultrasonic surgical instrument.
Figure 5B:
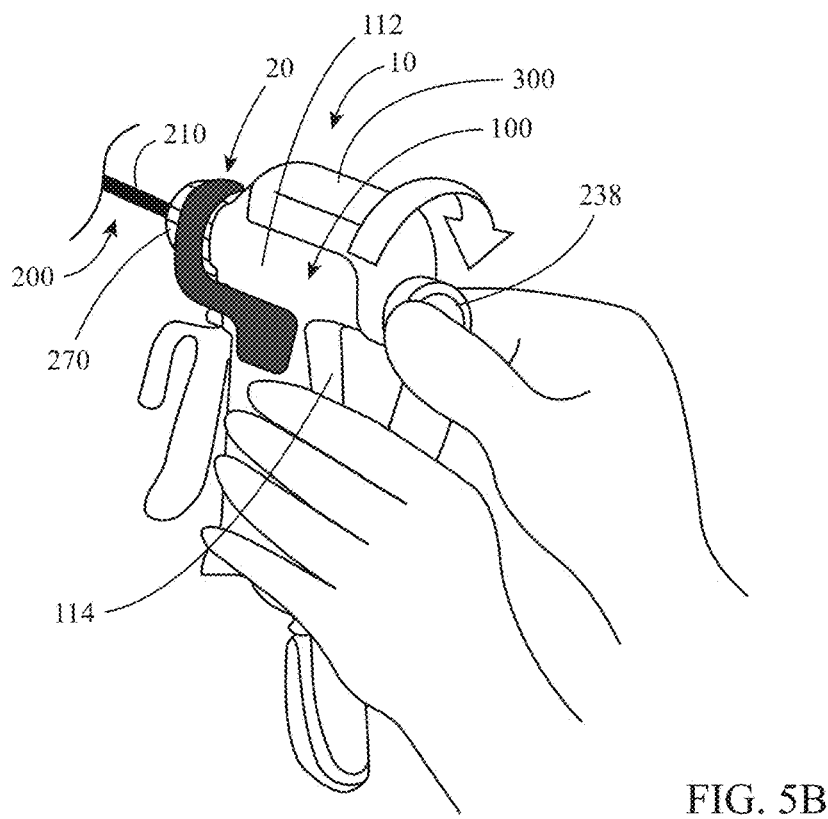
FIG. 5B is a rear, perspective view of the ultrasonic surgical instrument of FIG. 1 including the assembly tool of FIG. 3 engaged therewith, illustrating use of the assembly tool to facilitate engagement of the TAG with the ultrasonic surgical instrument.

In order to engage threaded female receiver 326 and threaded male shaft 237 with one another, the user grasps any suitable part of handle assembly 100, e.g., fixed handle portion 114, with one hand, and rotation knob 328 of TAG 300 with the other hand, as illustrated in FIG. 5B, and rotates rotation knob 328. As rotation knob 328 is rotated, threaded male shaft 237 is progressively engaged with threaded female receiver 326 until sufficient engagement is achieved, at which point integrated torque assembly 260 "slips" such that, upon further application of torque, threaded male shaft 237 and threaded female receiver 326 rotate together with one another, inhibiting further engagement therebetween. In embodiments where integrated torque assembly 260 is not provided, the above-detailed assembly is similar except that, rather than grasping rotation knob 328 directly, a separate torque wrench (not shown) is engaged about rotation knob 328 and utilized to rotate rotation knob 328. The separate torque wrench (not shown) is configured to "slip," inhibiting further rotation of the underlying rotation knob 238, once sufficient engagement of threaded male shaft 237 and threaded female receiver 326 is achieved.

Once ultrasonic transducer 230 and waveguide 230 are sufficiently engaged with one another, assembly tool 20 may be removed in the opposite manner as the engagement thereof detailed above, and battery assembly 400 may be inserted into compartment 116 of fixed handle portion 114 of housing 110 (if not done so previously) to complete the assembly of ultrasonic surgical instrument 10. Ultrasonic surgical instrument 10 may thereafter be used to perform one or more surgical tasks, e.g., to coagulate, cauterize, fuse, seal, cut, desiccate, and/or fulgurate tissue.

Once use of ultrasonic surgical instrument 10 is complete, and when it is desired to remove TAG 300 and/or elongated assembly 200 from handle assembly 100, assembly tool 20 may be re-engaged about ultrasonic surgical instrument 10. With assembly tool 20 engaged about ultrasonic surgical instrument 10, the user grasps any suitable part of handle assembly 100, e.g., fixed handle portion 114, with one hand, and rotation knob 328 of TAG 300 with the other hand, and rotates rotation knob 328 in the opposite direction until threaded female receiver 326 and threaded male shaft 237 are fully disengaged, at which point TAG 300 and/or elongated assembly 200 may be removed from handle assembly 100.

Referring generally to FIGS. 1-5B, assembly tool 20 may be provided separately from ultrasonic surgical instrument 10, may be provided together with ultrasonic surgical instrument 10, or may be included as part of a kit including portions of ultrasonic surgical instrument 10, e.g., a kit including TAG 300, handle assembly 100, and/or elongated assembly 200.

While several embodiments of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular embodiments. Those skilled in the art will envision other modifications within the scope and spirit of the claims appended hereto.

What is claimed is:

1. An assembly tool for removably coupling to a housing and a rotation knob of an ultrasonic surgical instrument, the assembly tool comprising:
    a body portion including a base and first and second legs extending from the base, the base and first and second legs defining a receiving area therebetween;
    a neck attached to the body portion; and
    a head portion attached to the neck, the head portion defining a central opening and at least one protrusion defined along an interior surface of the head portion,
    wherein the first and second legs of the body portion are configured to engage a portion of the housing of the ultrasonic surgical instrument when the portion of the housing is received within the receiving area, and wherein the at least one protrusion of the head portion is configured to engage a flute defined on an exterior surface of the rotation knob of the ultrasonic surgical instrument when the rotation knob is received within the central opening such that the rotation knob is restricted from rotating relative to the housing when the assembly tool is coupled to the ultrasonic surgical instrument.

2. The assembly tool according to claim 1, wherein the head portion includes first and second arms cooperating to define the central opening therebetween, the first and second arms including free ends defining a mouth therebetween, the mouth providing access to the central opening.

3. The assembly tool according to claim 2, wherein the first and second arms are movable to vary a width of the mouth.

4. The assembly tool according to claim 2, wherein the mouth opposes the neck.

5. The assembly tool according to claim 1, wherein the interior surface is shaped complementary to a shape of an exterior surface of the rotation knob of the ultrasonic surgical instrument.

6. The assembly tool according to claim 1, wherein the interior surface includes a plurality of alternating recesses and protrusions.

7. The assembly tool according to claim 1, wherein the receiving area is configured complementary to the portion of the housing of the ultrasonic surgical instrument.

8. The assembly tool according to claim 1, wherein the body portion, the neck, and the head portion are a single, monolithic component.

9. A kit, comprising:
    an ultrasonic surgical instrument including a housing and a rotation knob rotatable relative to the housing; and
    an assembly tool releasably engagable with the ultrasonic surgical instrument to prevent rotation of the rotation knob relative to the housing when the assembly tool is coupled to the ultrasonic surgical instrument, the assembly tool including:
        a body portion including a base and first and second legs extending from the base, the base and first and second legs defining a receiving area therebetween, the first and second legs of the body portion configured to receive a portion of the housing of the ultrasonic surgical instrument within the receiving area and to engage the portion of the housing of the ultrasonic surgical instrument when the portion of the housing is received within the receiving area;
        a neck attached to the body portion; and
        a head portion attached to the neck, the head portion defining a central opening and at least one protrusion defined along an interior surface of the head portion, the head portion configured to receive the rotation knob of the ultrasonic surgical instrument within the central opening and to engage a flute defined on an exterior surface of the rotation knob of the ultrasonic surgical instrument when the rotation knob is received within the central opening.

10. The kit according to claim 9, wherein the head portion of the assembly tool includes first and second arms cooperating to define the central opening, the first and second arms including free ends defining a mouth therebetween, the mouth providing access to the central opening.

11. The kit according to claim 10, wherein the ultrasonic surgical instrument includes an outer sleeve extending distally from the housing, the outer sleeve configured to pass through the mouth of the assembly tool and into the central opening of the assembly tool to enable engagement of the head portion of the assembly tool with the rotation knob of the ultrasonic surgical instrument.

12. The kit according to claim 11, wherein the first and second arms of the head portion of the assembly tool are configured to move to vary a width of the mouth of the assembly tool to facilitate passage of the outer sleeve of the ultrasonic surgical instrument through the mouth of the assembly tool.

13. The kit according to claim 11, wherein the first and second arms of the head portion of the assembly tool are configured to move to engage the rotation knob under bias.

14. The kit according to claim 9, wherein the rotation knob of the ultrasonic surgical instrument includes a plurality of spaced-apart flutes defined on the exterior surface thereof, and wherein the interior surface of the head portion of the assembly tool defines a plurality of spaced-apart protrusions configured for respective receipt within the plurality of spaced-apart flutes of the rotation knob of the ultrasonic surgical instrument.

15. The kit according to claim 9, wherein the receiving area of the body portion of the assembly tool is configured complementary to the portion of the housing of the ultrasonic surgical instrument.

16. The kit according to claim 9, wherein the first and second legs of the body portion of the assembly tool are configured to move to vary a width of the receiving area of the body portion of the assembly tool to facilitate receipt of the portion of the housing of the ultrasonic surgical instrument within the receiving area of the body portion of the assembly tool.

17. The kit according to claim 9, wherein the first and second legs of the body portion of the assembly tool are configured to move to engage the portion of the housing of the ultrasonic surgical instrument received within the receiving area of the body portion of the assembly tool under bias.

* * * * *